US012758502B2

(12) United States Patent
Cohen

(10) Patent No.: US 12,758,502 B2
(45) Date of Patent: *Oct. 13, 2026

(54) COMPOSITIONS AND METHODS OF USE

(71) Applicant: Strongbridge Dublin Limited, Trevose, PA (US)

(72) Inventor: Fredric Jay Cohen, Washington Crossing, PA (US)

( * ) Notice: Subject to any disclaimer, the term of this patent is extended or adjusted under 35 U.S.C. 154(b) by 1290 days.

This patent is subject to a terminal disclaimer.

(21) Appl. No.: 17/151,405

(22) Filed: Jan. 18, 2021

(65) Prior Publication Data

US 2021/0290542 A1 Sep. 23, 2021

Related U.S. Application Data

(63) Continuation-in-part of application No. PCT/US2020/037169, filed on Jun. 11, 2020, and a continuation-in-part of application No. PCT/US2020/014250, filed on Jan. 20, 2020, and a continuation-in-part of application No. PCT/US2019/063505, filed on Nov. 27, 2019, which is a continuation-in-part of application No. PCT/US2019/063507, filed on Nov. 27, 2019.

(60) Provisional application No. 62/863,125, filed on Jun. 18, 2019.

(51) Int. Cl.
*A61K 9/16* (2006.01)

(52) U.S. Cl.
CPC .......... *A61K 9/1652* (2013.01); *A61K 9/1611* (2013.01); *A61K 9/1623* (2013.01); *A61K 9/1635* (2013.01)

(58) Field of Classification Search
CPC .... A61K 31/18; A61K 9/1652; A61K 9/1611; A61K 9/1623; A61K 9/1635
See application file for complete search history.

(56) References Cited

U.S. PATENT DOCUMENTS 8,105,625 B2 1/2012 Rajewski
9,867,786 B2 1/2018 Crowley
2006/0182804 A1 8/2006 Burke
2012/0034272 A1 2/2012 Kuhl
2013/0122085 A1 5/2013 Dalton
2019/0169593 A1* 6/2019 Tarsio ..................... A23L 33/17
2020/0163911 A1 5/2020 Cohen

FOREIGN PATENT DOCUMENTS

WO 2020257037 12/2020

OTHER PUBLICATIONS

Sansone et. al. (Neurology (2016) 86:1408-1416) (Year: 2017).*
Clinicaltrails.gov NCT00494507 (2016) (Year: 2016).*
*The Novartis Pharmaceuticals Corp.* v. *Accord Healthcare, Inc.*, 21 F.4th 1362 (Fed. Cir. Jan. 3, 2022), Case No. 2021-1070. (Year: 2022).*
Kappos 2006 (p. S101, abstract P376). (Year: 2006).*
*Continental Can Co. USA* v. *Monsanto Co.*, 948 F.2d 1264, 1268 (Fed. Cir. 1991) (Year: 1991).*
Appeal 2017-010398 for U.S. Appl. No. 13/823,286 (Year: 2018).*
Pepcid® Prescribing Information (2011).*
Rambhade et al., *A Survey on Polypharmacy and Use of Inappropriate Medications*, 19 Toxicology Int'l 68-73 (2012).*
Pepcid® Prescribing Information (Jun. 2011). (Year: 2011).*
Keyevis™ Prescribing Information (Aug. 2015) (Year: 2015).*
Bhat et. al. (Indian Journal of Pharmaceutical Sciences (2005) 67:151-159). (Year: 2005).*
International Application No. PCT/US2020/037169; International Search Report and Written Opinion of the International Searching Authority, date of mailing Sep. 18, 2020; 9 pages.
Angeli; A. et al. "Famotidine, an Antiulcer Agent, Strongly Inhibits Helicobacter pylori and Human Carbonic Anhydrases" ACS Med. Chem. Lett. 2018, 9, 1035-1038.
Wulf; N. et al. "Sulfonamide cross-reactivity: Is there evidence to support broad cross-allergenicity?" Clinical Consultations, Am J Health-Syst Pharm—vol. 70 Sep. 1, 2013, 12 Pages.

* cited by examiner

*Primary Examiner* — Marcos L Sznaidman
(74) *Attorney, Agent, or Firm* — STERNE, KESSLER, GOLDSTEIN & FOX P.L.L.C.

(57) ABSTRACT

Provided is a pharmaceutical composition comprising: (a) granules comprising an active pharmaceutical ingredient, and one or more intragranular excipients; and an extragranular portion comprising at least one release modifier. Also provided are process for the preparation and methods for the use of the pharmaceutical composition.

1 Claim, No Drawings

COMPOSITIONS AND METHODS OF USE

Provided is a pharmaceutical composition comprising:

(a) granules comprising an active pharmaceutical ingredient and one or more intragranular excipients; and (b) an extragranular portion comprising at least one release modifier; wherein the release modifier is a hydroxypropyl methylcellulose or a mixture thereof, wherein the composition has a dissolution profile of at least about 80% mean drug release between about 6 hours and about 10 hours as measured using the paddle method (USP apparatus 2) with a stirring rate of 75 rotations per minute in 900 mL of phosphate buffer pH 8.0 with 0.5% hexadecyltrimethylammonium bromide at 37±0.5° C.

These and other aspects of the invention will be apparent upon reference to the following detailed description. To this end, various references are set forth herein which describe in more detail certain background information, procedures, compounds, and/or compositions, and are each hereby incorporated by reference in their entirety.

In the following description, certain specific details are set forth to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" or "some embodiments" or "a certain embodiment" means that a particular feature, structure or characteristic described for the embodiment is included in at least one embodiment. Thus, the appearances of the phrases "in one embodiment" or "in an embodiment" or "in some embodiments" or "in a certain embodiment" in various places throughout this specification are not necessarily all referring to the same embodiment. Furthermore, the particular features, structures, or characteristics may be combined in any suitable manner in one or more embodiments.

Also, as used in this specification and the appended claims, the singular forms "a," "an," and "the" include plural referents unless the content clearly dictates otherwise.

The term "and/or" when in a list of two or more items, means that any of the listed items can be employed by itself or in combination with one or more of the listed items. For example, the expression "A and/or B" means either or both of A and B, i.e. A alone, B alone or A and B in combination. The expression "A, B and/or C" is intended to mean A alone, B alone, C alone, A and B in combination, A and C in combination, B and C in combination or A, B, and C in combination.

When ranges of values are disclosed, and the notation "from $n_1$ . . . to $n_2$" or "between $n_1$ . . . and $n_2$" is used, where $n_1$ and $n_2$ are the numbers, then unless otherwise specified, this notation is intended to include the numbers themselves and the range between them. This range may be integral or continuous between and including the end values. By way of example, the range "from 1 to 3 μM (micromolar)" is intended to include 1 μM, 3 μM, and everything in between to any number of significant figures (e.g., 1.255 μM, 2.1 μM, 2.9999 μM, etc.).

As used herein, the term "about" qualifies the numerical values that it modifies, denoting such a value as variable within a margin of error. When no margin of error, such as a standard deviation to a mean value given in a chart or table of data, is recited, the term "about" means that range which would encompass the recited value and the range which would be included by rounding up or down to that figure, considering significant figures.

As used herein, the term "disease" is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

As used herein, "effective amount" and "therapeutically effective amount" of an agent, compound, drug, composition or combination is an amount which is nontoxic and effective for producing some desired therapeutic effect upon administration to a subject or patient (e.g., a human subject or patient). The precise therapeutically effective amount for a subject may depend upon, e.g., the subject's size and health, the nature and extent of the condition, the therapeutics or combination of therapeutics selected for administration, and other variables known to those of skill in the art. The effective amount for a given situation is determined by routine experimentation and is within the judgment of the clinician.

As used herein, "patient" or "individual" or "subject" means a mammal, including a human, for whom or which therapy is desired, and generally refers to the recipient of the therapy.

As used herein, "active pharmaceutical ingredient" or "API" means any substance or mixture of substances intended to be used in the manufacture of a drug product and that, when used in the production of a drug, becomes an active ingredient in the drug product. Such substances are intended to furnish pharmacological activity or other direct effect in the diagnosis, cure, mitigation, treatment or prevention of disease or to affect the structure and function of the body. An active pharmaceutical ingredient also may be referred to as a drug substance.

As used herein, a patient is said to "tolerate" a dose of a compound if administering that dose to that patient does not result in an unacceptable adverse event or an unacceptable combination of adverse events. One of skill in the art will appreciate that tolerance is a subjective measure and that what may be tolerable to one patient may not be tolerable to a different patient. For example, one patient may not be able to tolerate headache, whereas a second patient may find headache tolerable but is not able to tolerate vomiting, whereas for a third patient, either headache alone or vomiting alone is tolerable, but the patient is not able to tolerate the combination of headache and vomiting, even if the severity of each is less than when experienced alone.

As used herein, "pharmaceutically acceptable" refers to a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration.

"Pharmacologically active" (or simply "active") as in a "pharmacologically active" (or "active") derivative or analog, refers to a derivative or analog having the same type of pharmacological activity as the parent compound and approximately equivalent in degree. The term "pharmaceutically acceptable salts" include acid addition salts which are formed with inorganic acids or organic acids. Salts formed with the free carboxyl groups can also be derived from inorganic bases and organic bases. Lists of suitable salts are found in *Remington's Pharmaceutical Sciences,* 17.sup.th Ed., (Mack Publishing Company, Easton, 1985), p. 1418, Berge et al., J. Pharm. Sci., 1977, 66 (1), 1-19 and in Stahl et al., *Handbook of Pharmaceutical Salts: Properties, Selection, and Use*, (Wiley, 2002).

Pharmaceutically acceptable salts can be formed from, for example, the following acids: 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); ascorbic acid (D); aspartic acid (L); aspartic acid (D); benzenesulfonic acid; benzoic acid; camphoric acid (+); camphoric acid (−); camphor-10-sulfonic acid (+); camphor-10-sulfonic acid (−); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); glucoheptonic acid (L); gluconic acid (D); gluconic acid (L); glucuronic acid (D); glucuronic acid (L); glutamic acid; glutaric acid; glycerophosphoric acid; glycolic acid; hippuric acid; hydrobromic acid; hydrochloric acid; isobutyric acid; lactic acid (DL); lactobionic acid; lauric acid; maleic acid; malic acid (−L); malic acid (D); malonic acid; mandelic acid (DL); methanesulfonic acid; naphthalene-1,5-disulfonic acid; naphthalene-2-sulfonic acid; nicotinic acid; nitric acid; oleic acid; oxalic acid; palmitic acid; pamoic acid; phosphoric acid; proprionic acid; pyroglutamic acid (−L); pyroglutamic acid (D); salicylic acid; sebacic acid; stearic acid; succinic acid; sulfuric acid; tartaric acid (+L); tartaric acid (D); thiocyanic acid; toluenesulfonic acid (p); and/or undecylenic acid.

Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

The phrase "therapeutically effective" is intended to qualify the amount of active ingredients used in the treatment of a disease or disorder or on the effecting of a clinical endpoint.

The term "therapeutically acceptable" refers to those compounds (or salts, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. Treatment may also be preemptive in nature, i.e., it may include prevention of disease. Prevention of a disease may involve complete protection from disease, for example as in the case of prevention of infection with a pathogen or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

As used herein, "up-titration" of a compound refers to increasing the amount of a compound to achieve a therapeutic effect that occurs before dose-limiting intolerability for the patient. Up-titration can be achieved in one or more dose increments, which may be the same or different.

As used herein, the term "stable" with respect to pharmaceutical compositions, the pharmaceutical composition exhibits total impurities not more than 1.0% at ambient temperature (15-25° C.) and 75% relative humidity, when stored in high density polyethylene (HDPE) container for 7 or 35 days.

As used herein, the term "solid dosage form" or "dosage form" or "composition" as used herein means a solid dosage form suitable for administration, such as a tablet, capsule, spheroids, mini-tablets, pellets, granules, pills and the like.

As used herein, the term "filler" means an inert substance used to create the desired bulk, flow properties, and compression characteristics in the preparation of pharmaceutical composition.

As used herein, the term "binder" means an inert substance used to ensure that granules and/or tablets can be formed with the required mechanical strength and hold a tablet together after it has been compressed, preventing it from breaking down into its component powders during packaging, shipping and routine handling.

As used herein, the term "glidant" means an inert substance used to promote the flowability of a granulation.

As used herein, the term "low to medium" viscosity means a viscosity in the range of from about 15 mPas to about 1000 mPas. It is recognized in the art that determining the viscosity of cellulosic derivatives is based upon standard techniques and grading in the art e.g. for HPMC, viscosity may be determined at 20° C. with a 2% solution using a Ubbelohde viscometer.

Provided is a pharmaceutical composition comprising:

(a) granules comprising an active pharmaceutical ingredient, such as dichlorphenamide, or a pharmaceutically acceptable salt thereof, and one or more intragranular excipients; and (b) an extragranular portion comprising at least one release modifier; wherein the release modifier is a hydroxypropyl methylcellulose or a mixture thereof, wherein the composition has a dissolution profile of at least about 80% mean drug release between about 6 and 10 hours as measured using the paddle method (USP apparatus 2) with a stirring rate of 75 rotations per minute in 900 mL of phosphate buffer pH 8.0 with 0.5% hexadecyltrimethylammonium bromide at 37±0.5° C.

The pharmaceutical composition is a solid dosage form intended for oral administration. In some embodiments, the pharmaceutical composition is a tablet.

In some embodiments, the granules comprise dichlorphenamide, or a pharmaceutically acceptable salt thereof in an amount between about 25 mg and about 200 mg. In some embodiments, the granules comprise dichlorphenamide, or a pharmaceutically acceptable salt thereof in an amount between about 100 mg and about 200 mg. In some embodiments, the granules comprise 25 mg dichlorphenamide, or a pharmaceutically acceptable salt thereof. In some embodiments, the granules comprise 50 mg dichlorphenamide, or a pharmaceutically acceptable salt thereof. In some embodiments, the granules comprise 100 mg dichlorphenamide, or a pharmaceutically acceptable salt thereof. In some embodiments, the granules comprise 200 mg dichlorphenamide, or a pharmaceutically acceptable salt thereof.

In some embodiments, the dichlorphenamide, or a pharmaceutically acceptable salt thereof is present in the granules in an amount of between about 50% w/w and about 70% w/w. In some embodiments, the dichlorphenamide, or a pharmaceutically acceptable salt thereof is present in the granules in an amount of between about 60% w/w and about 65% w/w. In some embodiments, the dichlorphenamide, or a pharmaceutically acceptable salt thereof is present in the granules in an amount of about 62% w/w.

In some embodiments, the dichlorphenamide, or a pharmaceutically acceptable salt thereof is present in the pharmaceutical composition in an amount of between about 15% w/w and about 45% w/w. In some embodiments, the dichlorphenamide, or a pharmaceutically acceptable salt thereof is present in the pharmaceutical composition in an amount of between about 15% w/w and about 25% w/w. In some embodiments, the dichlorphenamide, or a pharmaceutically acceptable salt thereof is present in the pharmaceutical composition in an amount of about 20% w/w. In some embodiments, the dichlorphenamide, or a pharmaceutically acceptable salt thereof is present in the pharmaceutical composition in an amount of between about 35% w/w and about 45% w/w. In some embodiments, the dichlorphenamide, or a pharmaceutically acceptable salt thereof is present in the pharmaceutical composition in an amount of about 40% w/w.

In some embodiments, the one or more intragranular excipients are chosen from fillers, binders, and glidants.

In some embodiments, the one or more fillers are chosen from dibasic calcium phosphate, tribasic calcium phosphate, carmellose, sugar alcohols (such as mannitol, sorbitol, and xylitol), kaolin, lactose, sucrose, mannitol, cellulose, calcium carbonate, magnesium carbonate, starch, mixtures of isomaltulose derivatives (such as galenIQ), and mixtures thereof.

In some embodiments, the filler is lactose. In certain embodiments, the lactose is chosen from lactose monohydrate (such as Lactose FastFlo), lactose DT (direct tableting), lactose anhydrous, spray-dried monohydrate lactose, lactose-316 Fast Flo, microcrystalline cellulose co-processed with other excipients (such as microcrystalline cellulose coprocessed with lactose mono hydrate (MicroceLac 100) and microcrystalline cellulose co-processed with colloidal silicon dioxide (SMCCSO, Prosolv 50 and Prosolv HD 90), and mixtures thereof. In some embodiments, lactose is lactose monohydrate. The lactose monohydrate is amorphous, crystalline or a mixture thereof.

In some embodiments, the filler is starch. In certain embodiments, the starch is chosen from maize starch, potato starch, rice starch, wheat starch, pregelatinized starch, and mixtures thereof.

In some embodiments, the filler is cellulose. In certain embodiments, the cellulose is chosen from crystalline celluloses, powdered celluloses, and mixtures thereof. In some embodiments, crystalline cellulose is microcrystalline cellulose (such as such as Avicel PH 101, Avicel PH102, Avicel PH 200, Avicel PH 105, Avicel DG, Ceolus KG 802, Ceolus KG 1000, SMCCSO and Vivapur 200).

In some embodiments, the one or more fillers is a mixture of microcrystalline cellulose and lactose monohydrate.

In some embodiments, the one or more fillers is present in the granules in an amount of between about 20% w/w and about 40% w/w. In some embodiments, the one or more fillers is present in the granules in an amount of between about 25% w/w and about 35% w/w. In some embodiments, the one or more fillers is present in the granules in an amount of about 30% w/w.

In some embodiments, the one or more fillers is present in the pharmaceutical composition in an amount of between about 15% w/w and about 50% w/w. In some embodiments, the one or more fillers is present in the pharmaceutical composition in an amount of between about 15% w/w and about 25% w/w. In some embodiments, the one or more fillers is present in the pharmaceutical composition in an amount of about 19% w/w. In some embodiments, the one or more fillers is present in the pharmaceutical composition in an amount of between about 35% w/w and about 45% w/w. In some embodiments, the one or more fillers is present in the pharmaceutical composition in an amount of about 42% w/w.

In some embodiments, the one or more binders are chosen from hydroxypropyl celluloses in various grades, hydroxypropyl methylcelluloses in various grades, polyvinylpyrrolidones in various grades, copovidones, powdered acacia, gelatin, guar gum, carbomers, methylcelluloses, polymethacrylates, starches, and mixtures thereof.

In some embodiments, the binder is starch. In certain embodiments, the starch is chosen from maize starch, potato starch, rice starch, wheat starch, pregelatinized starch, and mixtures thereof. In some embodiments, starch is pregelatinized starch.

In some embodiments, the one or more binders is present in the granules in an amount of between about 5% w/w and about 15% w/w. In some embodiments, the one or more binders is present in the granules in an amount of between about 7% w/w and about 10% w/w.

In some embodiments, the one or more binders is present in the pharmaceutical composition in an amount of between about 2% w/w and about 10% w/w. In some embodiments, the one or more binders is present in the granules in an amount of between about 2% w/w and about 5% w/w.

In some embodiments, the one or more glidants are chosen from talc, colloidal silica (colloidal silicon dioxide), cornstarch, calcium silicate, magnesium silicate, colloidal silicon, silicon hydrogel, and mixtures thereof.

In some embodiments, the one or more glidants is colloidal silica, such as anhydrous colloidal silica.

In some embodiments, the one or more glidants is present in the granules in an amount of between about 0% w/w and about 2% w/w. In some embodiments, the one or more glidants is present in the granules in an amount of between about 0.3% w/w and about 0.5% w/w.

In some embodiments, the one or more glidants is present in the pharmaceutical composition in an amount of between about 0 and about 2% w/w. In some embodiments, the one or more glidants is present in the pharmaceutical composition in an amount of between about 0.3 and about 0.5% w/w.

In some embodiments, the release modifier is a hydroxypropyl methylcellulose or a mixture thereof chosen from low to medium viscosity hydroxypropyl methylcellulose and mixtures thereof. In some embodiments, the release modifier is a hydroxypropyl methylcellulose or a mixture thereof chosen from Methocel E, Methocel E3, Methocel E5, Methocel E6, Methocel E15, Methocel E50, Methocel K, Methocel K3, Methocel K4M, Methocel K15M, Methocel K100LV, Methocel K100M, Methocel, Hypromellose type 1828, Hypromellose type 2208, Hypromellose type 2906, Hypromellose type 2910, Metolose 60SH (Type 2910), Metolose 65SH (Type 2906), Metolose 90SH (Type 2208), Methocel A, Methocel A15, Methocel A4C, Methocel A15C, Methocel A4M, Metolose SM, and mixtures thereof. In some embodiments, the release modifier is chosen from Hypromellose K100LV and Hypromellose E50, and mixtures thereof. In some embodiments, the release modifier is a mixture of Hypromellose K100LV and Hypromellose E50.

In some embodiments, the release modifier is present in the pharmaceutical composition in an amount of between about 30% w/w and about 40% w/w. In some embodiments, the release modifier is present in the pharmaceutical composition in an amount of about 35% w/w.

In some embodiments, the extragranular portion further one or more extragranular excipients. In some embodiments, the one or more extragranular excipients comprises one or more lubricants. Lubricants can be present in an amount of about 0% w/w to about 10% by weight. Non-limiting examples of lubricants include magnesium stearate, stearic acid (stearin), hydrogenated oil, polyethylene glycol, sodium stearyl fumarate, and glyceryl behenate. In some embodiments, the lubricant is magnesium stearate.

In some embodiments, the one or more extragranular excipients comprises one or more fillers.

In some embodiments, the granules comprise:
an active pharmaceutical ingredient;
microcrystalline cellulose;
lactose monohydrate;
pregelatinized starch; and
colloidal silica.

In some embodiments, the extragranular portion comprises: hydroxypropyl methylcellulose or a mixture thereof;
microcrystalline cellulose;
colloidal silica; and
magnesium stearate.

In some embodiments, the patient may receive a dose of between 50 mg twice daily and 100 mg twice daily. In some embodiments, the dose is 50 mg once daily. In some embodiments, the dose is 50 mg once every other day. In some embodiments, the dose is 25 mg once daily. In some embodiments, the dose is 25 mg once every other day.

In some embodiments, the therapeutically effective amount of the dichlorphenamide, or a pharmaceutically acceptable salt thereof, is between 25 mg and 200 mg per day.

In some embodiments, the therapeutically effective amount of the dichlorphenamide, or a pharmaceutically acceptable salt thereof, is 50 mg twice daily.

In some embodiments, the dichlorphenamide, or a pharmaceutically acceptable salt thereof, is administered via a titration scheme that comprises the up-titration of the dichlorphenamide, or a pharmaceutically acceptable salt thereof, at weekly intervals until a modified dose is administered. In some embodiments, the modified dose of the dichlorphenamide, or a pharmaceutically acceptable salt thereof, is 200 mg.

Also provided is a method of treating primary hyperkalemic periodic paralysis, primary hypokalemic periodic paralysis, or related variants in a patient in need thereof, comprising administering to the patient, a pharmaceutical composition described herein. Also provided is a method for treating a disease chosen from primary hyperkalemic periodic paralysis, primary hypokalemic periodic paralysis, and related variants in a subject in need thereof, wherein the subject is being administered an organic anion transporter-1 (OAT1) substrate for the treatment of a disease or disorder, the method comprising: discontinuing administration of the OAT1 substrate, and administering to the subject a therapeutically effective amount of dichlorphenamide, or a pharmaceutically acceptable salt thereof, thereby avoiding the use of dichlorphenamide, or a pharmaceutically acceptable salt thereof in combination with the OAT1 substrate. The concomitant administration of dichlorphenamide may increase the mean plasma elimination half-life of a number of drugs that are OAT1 substrates, leading to increased plasma concentrations. In certain embodiments, the OAT1 substrate is a drug that is sensitive to OAT1 inhibition. As used herein, "sensitive" means that in the presence of a potent OAT1 inhibitor, the blood levels of the substrate increase to a clinically relevant extent. In certain embodiments, the OAT1 substrate is chosen from methotrexate, famotidine, and oseltamivir. See, e.g., PCT/US19/63505, filed Nov. 27, 2019; PCT/US2019/063507, filed Nov. 27, 2019; and PCT/US2020/014250, filed Jan. 20, 2020, each of which is incorporated by reference for all purposes. See, also, U.S. application Ser. No. 16/201,410, filed Nov. 27, 2018, Ser. No. 16/780,057, filed Feb. 3, 2020, Ser. No. 16/535,704, filed Aug. 8, 2019, Ser. No. 16/205,602, filed Nov. 30, 2018, Ser. No. 16/540,447, filed Aug. 14, 2019, Ser. No. 16/540,450, filed Aug. 14, 2019, Ser. No. 16/540,456, filed Aug. 14, 2019, Ser. No. 16/540,461, filed Aug. 14, 2019, Ser. No. 16/540,464, filed Aug. 14, 2019, Ser. No. 16/540,468, filed Aug. 14, 2019, Ser. No. 16/253,515, filed Jan. 22, 2019, and Ser. No. 16/535,692, filed Aug. 8, 2019, each of which is incorporated by reference for all purposes.

In some embodiments, the disease chosen from primary hyperkalemic periodic paralysis, primary hypokalemic periodic paralysis, and related variants; Aland Island eye disease atrial fibrillation, Brugada syndrome, cardiomyopathy, cerebellar syndrome, cone-rod dystrophy, cystoid macular edema of retinitis pigmentosa, Dravet syndrome, epilepsy, epileptic encephalopathy, episodic ataxia, myokymia syndrome, episodic pain syndrome, hemiplegic migraine, febrile seizures, heart block, intracranial hypertension, long QT syndrome, neuropathy, night blindness, paroxysmal exercise-induced dyskinesia, Rett syndrome, sick sinus syndrome, spinocerebellar ataxia, sudden infant death syndrome (SIDS), Timothy syndrome, and ventricular fibrillation.

In some embodiments, the disease chosen from primary hyperkalemic periodic paralysis, primary hypokalemic periodic paralysis, and related variants. In some embodiments, the disease primary hyperkalemic periodic paralysis. In some embodiments, the disease is primary hypokalemic periodic paralysis. In some embodiments, the disease is a related variant to primary hyperkalemic periodic paralysis. In some embodiments, the disease is a related variant to primary hypokalemic periodic paralysis.

In some embodiments, the disease is Aland Island eye disease. In some embodiments, the disease is atrial fibrillation, such as familial atrial fibrillation. In some embodiments, the disease is Brugada syndrome, such as type 1 or type 3. In some embodiments, the disease is cardiomyopathy, such as dilated cardiomyopathy. In some embodiments, the disease is cerebellar syndrome in phosphomannomutase 2 (PMM2) deficiency, a congenital disorder of glycosylation. In some embodiments, the disease is cone-rod dystrophy, such as X-linked cone-rod dystrophy. In some embodiments, the disease is cystoid macular edema of retinitis pigmentosa. In some embodiments, the disease is Dravet syndrome. In some embodiments, the disease is epilepsy, such as generalized epilepsy, epilepsy type two, or epilepsy with febrile seizures. In some embodiments, the disease is epileptic encephalopathy, early infantile epileptic encephalopathy, which is an autosomal dominant form of the disease. In some embodiments, the disease is episodic ataxia, such as type 1, type 2, or type 5, or myokymia syndrome. In some embodiments, the disease is episodic pain syndrome, such as familial episodic pain syndrome. In some embodiments, the disease is hemiplegic migraine types, familial hemiplegic migraine types 1 and 3. In some embodiments, the disease is febrile seizures, such as familial febrile seizures. In some embodiments, the disease is heart block, such as nonprogressive heart block, and progressive heart block type IA. In some embodiments, the disease is intracranial hypertension, such as idiopathic intracranial hypertension. In some embodiments, the disease is long QT syndrome-3. In some embodiments, the disease is neuropathy, hereditary neuropathy, sensory neuropathy, and autonomic neuropathy type VII. In some embodiments, the disease is night blindness, such as congenital stationary night blindness, and X-linked night blindness. In some embodiments, the disease is paroxysmal exercise-induced dyskinesia. In some embodiments, the disease is Rett syndrome. In some embodiments, the disease is sick sinus syndrome. In some embodiments, the disease is spinocerebellar ataxia, such as spinocerebellar ataxia type 6. In some embodiments, the disease is sudden infant death syndrome (SIDS). In some embodiments, the disease is Timothy syndrome. In some embodiments, the disease is ventricular fibrillation, such as familial ventricular fibrillation.

Also provided is a process for the production of a pharmaceutical composition of any one of the preceding claims comprising:

mixing the granules comprising the active pharmaceutical ingredient, the at least one release modifier, and optionally, the one or more extragranular excipients to form a tablet blend; and compressing the tablet blend to form a tablet.

In some embodiments, the granules are prepared by a process comprising: wet granulating a mixture of the active pharmaceutical ingredient, and the one or more intragranular excipients; and drying the wet granules.

The various embodiments described above can be combined to provide further embodiments. All references, including the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments. The discussion of those references is intended merely to summarize the assertions made by their authors. No admission is made that any reference (or a portion of any reference) is relevant prior art (or prior art at all). Applicant reserves the right to challenge the accuracy and pertinence of the cited references.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations, or methods, or any combination of such changes and modifications of use of the invention, may be made without departing from the spirit and scope thereof.

What is claimed is:

1. A method of administering dichlorphenamide to treat primary hyperkalemic periodic paralysis or primary hypokalemic periodic paralysis in a human subject in need thereof, wherein the subject is being administered famotidine for the treatment of a disease or disorder, the method comprising:

discontinuing administration of the famotidine to the subject, and administering dichlorphenamide in tablet form to the subject at an initial dose of 50 mg, once or twice daily, thereby avoiding concomitant administration of famotidine and dichlorphenamide to the subject.

* * * * *